US008771181B2

(12) United States Patent
Garcia-Bengochea (10) Patent No.: US 8,771,181 B2
(45) Date of Patent: Jul. 8, 2014

(54) SURGICAL RETRACTOR EXTENSIONS (76) Inventor: Javier Garcia-Bengochea, Jacksonville, FL (US)

( * ) Notice: Subject to any disclaimer, the term of this patent is extended or adjusted under 35 U.S.C. 154(b) by 37 days.

(21) Appl. No.: 13/533,330

(22) Filed: Jun. 26, 2012

(65) Prior Publication Data

US 2012/0265019 A1    Oct. 18, 2012

Related U.S. Application Data (62) Division of application No. 12/635,902, filed on Dec. 11, 2009, which is a division of application No. 11/316,858, filed on Dec. 23, 2005, now abandoned.

(60) Provisional application No. 60/742,071, filed on Dec. 2, 2005, provisional application No. 60/691,141, filed on Jun. 16, 2005.

(51) Int. Cl.
A61B 1/32        (2006.01)
A61B 17/02       (2006.01)

(52) U.S. Cl.
CPC ..................................... A61B 17/02 (2013.01)
USPC ............................ 600/208; 600/204; 600/210

(58) Field of Classification Search
USPC .................................. 600/188, 204, 208, 210
See application file for complete search history.

(56) References Cited

FOREIGN PATENT DOCUMENTS

WO    WO 2006/422241 A2 *   4/2006

* cited by examiner

Primary Examiner — Andrew Yang
(74) Attorney, Agent, or Firm — Thomas C. Saitta (57) ABSTRACT A surgical retractor apparatus having one or more independent, removable extension members adapted to be mounted at the distal end of the retractor, or between the blades of a spreadable retractor, after the retractor has been positioned in the patient, such that a significant portion of the extension member extends beyond the distal end of the retractor to preclude or minimize intrusion of tissue into the access area created by the retractor. The extension members may vary in size and shape so that the most appropriate extension member can be chosen to address the intrusion problem, and the extension members may be mounted at various fixed locations, using clips, mechanical interlocking structures or the like.

20 Claims, 6 Drawing Sheets

SURGICAL RETRACTOR EXTENSIONS

This application is a divisional application of U.S. patent application Ser. No. 12/653,902, filed Dec. 18, 2009, claiming the benefit of U.S. patent application Ser. No. 11/316,858, filed Dec. 23, 2005, now abandoned, claiming the benefit of U.S. Provisional Patent application Ser. No. 60/691,141, filed Jun. 16, 2005, and U.S. Provisional Application Ser. No. 60/742,071, filed Dec. 2, 2005, the disclosures of which are incorporated herein by reference.

BACKGROUND OF THE INVENTION

This invention relates generally to the field of devices utilized in surgery to retract and retain tissue, organs or the like to provide the surgeon with access or an unobstructed pathway to an organ, bone, tissue or point in the body. Such devices are typically referred to generically as retractors. More particularly, the invention relates to retractors utilized with minimally invasive surgical techniques, wherein minimally sized openings are created in the body rather than relatively large incisions. Tubular devices known as cannula retractors, or spreading retractors having finger-like extensions or blades, are inserted into the small opening and through or around the body tissues, muscles, tendons, ligaments, etc., thereby minimizing damage to the body. The surgeon then performs the necessary procedure through the retractor tube using specially designed tools and equipment.

A problem with known retractors used in minimally invasive surgery is that the distal end profile or configuration of the device is fixed. A typical tubular retractor has a circular or elliptical transverse cross-section with the distal end lying in the plane perpendicular or slanted relative to the longitudinal axis. Other tubular distractors may have non-planar ends of varying configurations, such as having a spatula-like extension. Spreading retractors likewise have varying end configurations. Because the distal end configurations of the devices are fixed, the devices often fail to prevent creep or herniation of tissue at or around the distal end of the device, and this tissue creep can interfere with the necessary physical or visual access. This is particularly true when the distal end of the retractor device is positioned adjacent or near a bone, such as a vertebra for example, that does not have a planar or smooth outer contour, or where the retractor device is disposed at a non-perpendicular angle to the bone. In these circumstances it often becomes necessary for the surgeon to cut away the interfering tissue, thereby creating additional tissue damage that needs to heal and increasing the possibility of detrimental results such as bleeding, increased pain, infection and the like.

One attempted solution that is found in certain retractors of the spreadable blade type is to provide shim members that are mounted in interior channels disposed in each of the blades. The shim can be extended beyond the distal end of the blade by sliding the shim relative to the blade. The shortcomings of this solution to the problem of tissue creep is that the location of the shims are determined by the location of the blades after they have been positioned and spread. Thus, the surgeon cannot address the problem of tissue creep that occurs between the blades.

The invention at hand addresses this tissue creep problem by providing a retractor device for minimally invasive surgery that incorporates extension members in the form of shields or barriers that are selectively attached at, adjacent or to the end of a tubular retractor, and to the ends or sides of blade-type spreadable retractors, so as to extend therefrom in order to fill any gaps between the distal end or side of the retractor and the bone, organ or other body component of concern, such that tissue is precluded from creeping or herniating into the gap. The extensions may be mounted to the retractor at any point about or adjacent the distal end utilizing various mechanical joining techniques, and the extensions may vary in shape, size, thickness and other characteristics. The extensions may be preformed with a fixed curvature so as to match the interior curvature of the retractor, or they may be composed of a flexible material such that they adapt to the interior curvature of the retractor upon affixation. The extensions may be provided with teeth, apertures, slits or the like to better prevent tissue creep.

Specialized applicator equipment or tools are preferably provided that allow the surgeon to grasp or secure a particular extension, to insert the extension into and down the retractor, and to affix the extension to the interior wall or distal end of the retractor. Such equipment may take the form of forceps that retain the extension member during insertion and placement within the tubular retractor or other retractor blade.

SUMMARY OF THE INVENTION

The invention is a retractor device for minimally invasive surgery that incorporates independent, discrete, removable extension members in the form of shields or barriers that are selectively attached at, adjacent or to the end of a tubular retractor, or at, adjacent or to the ends or sides of blade retractors, so as to extend therefrom in order to fill any gaps between the distal end of the retractor and the bone, organ or other body component of concern, such that tissue is precluded from creeping or herniating into the gap. The extensions may be mounted to the retractor at multiple chosen locations utilizing various mechanical interlocking, clipping or similar joining techniques, and the extensions may vary in shape, size, thickness and other characteristics. The extensions may be preformed with a fixed curvature so as to match the interior curvature of the retractor, or they may be composed of a flexible material such that they adapt to the interior curvature of the retractor upon affixation. The extensions may be provided with teeth, apertures, slits or the like to better prevent tissue creep. The extensions are attached to the retractor after the retractor has been positioned in the patient.

In a preferred embodiment, the extension members are clipped to the end or exposed edge of a tubular retractor, or to the ends, sides or exposed edges of a blade retractor, using a generally J- or U-shaped clip member located on the extension member. In an alternative embodiment the extension member comprises a compressible slotted annular band whereby the J- or U-shaped clip extension member is retained against the inner wall of the tubular retractor by biasing forces.

Specialized equipment or tools allow the surgeon to grasp or secure one or more chosen extensions, to insert the extension into and down the retractor, and to affix the extension to the interior wall or distal end of the retractor. In a preferred embodiment, the applicator or insertion tool comprises a forceps-type device having a means to temporarily retain one or two extension members on a pair of extended L-shaped arms, wherein squeezing a pair of handles results in separation of the L-shaped arms.

It is contemplated that the invention may be provided to surgeons in the form of a kit, such kit comprising a plurality of extension members of varying shapes and sizes, an applicator tool, and possibly a depth gauge.

DETAILED DESCRIPTION OF THE INVENTION

With reference to the drawings, the invention will now be described in detail with regard for the best mode and the preferred embodiments. The invention is a surgical retractor apparatus or assembly and its method of use, the surgical retractor assembly having selectable extension members that are mounted or affixed at, on, to or adjacent the distal end of a tubular retractor member, or the ends or sides of a spreadable blade retractor, such that the distal profile or configuration can be altered to better match the contour of the bone, organ or other body component or better still the shape of a portion of the open area between the distal end of the retractor and the bone, organ or other body component, so as to preclude or minimize intrusion of tissue or other matter by creep or herniation into the access passageway defined by the retractor. The extension members are independent, discrete and removable members, and are attached to the retractor after the retractor has been inserted into the patient. The illustrations show a tubular retractor member that is circular in transverse cross-section, but it is to be understood that it is contemplated that a tubular retractor of elliptical or other cross-sectional configuration may also be utilized. Likewise, it is also to be understood that it is contemplated that the retractor may also comprise one of the type having one or more spreadable blades or finger-like sections, each of the blades or sections having a distal end of fixed configuration, in which case the extension members may be positioned on the sides of the blades as well as on the ends.

The apparatus comprises a retractor member 10 comprising a generally elongated main body 11 of relatively small transverse dimension having a proximal end 12 and a distal end 13, wherein the distal end 13 is adapted to be inserted into the body through a relatively small incision or opening, whereby an access pathway is created that enables the surgeon to visualize and perform procedures in the interior of the patient. The length of the main body 11 is chosen such that the proximal end 12 remains disposed externally to the body during the procedure. The retractor member 10 may comprise a tubular main body 11 that is circular in transverse cross-section, with the distal end 13 and proximal end 12 lying in planes perpendicular to the longitudinal axis. Alternatively, the main body 11 may be elliptical or otherwise non-circular in cross-section, and the distal end 13 and proximal end 12 may be disposed in non-perpendicular planes or may have non-planar configurations, such as for example when a spatula-like configuration is provided on the distal end 13.

Figure 7:
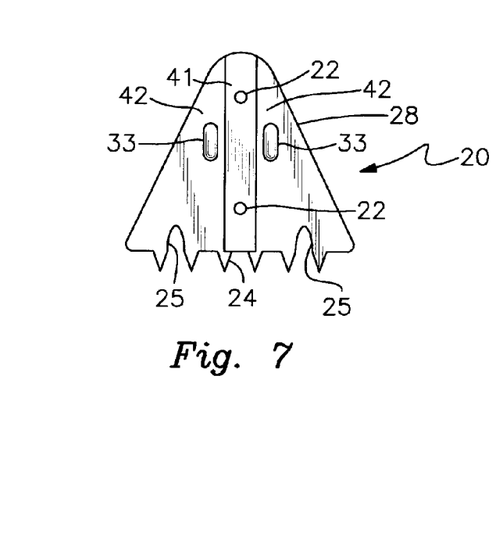
FIG. 7 is a front view of another alternative embodiment of the extension member having a pair of mounting clips, teeth and slots.
Figure 8:
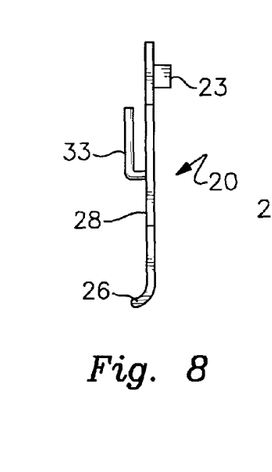
FIG. 8 is a side view of another alternative embodiment of the extension member having a grasping protrusion and a lip member.

The extension members 20 are independent, discrete, removable members distinct from the retractor member 10 and may be composed of varying materials and comprise a shielding main body 28 having varying shapes and sizes. Preferably, the extension members 20 are relatively thin so as to only minimally diminish the size of the access opening provided by the retractor member 10. In a preferred embodiment, the extension members 20 are composed of a plastic material such that the main body 28 is able to flex so as to conform to the interior curvature of the retractor member 10 when mounted thereon. For example, the extension member main bodies 28 may be relatively planar prior to connection to the retractor member 10, becoming curved upon being forced against the retractor member 10 for attachment. Alternatively, the mains bodies 28 of the extension members 28 may be formed with a relatively rigid central portion 41 acting in the form of a "backbone", with relatively flexible lateral portions 42 extending to either side of the central portion 41, as shown in FIG. 7. The central portion 41 may be formed as a thicker region, may be composed of a different material possessing more rigidity than the material composing the lateral portions 42, or may comprise ridges or similar reinforcing structures. Furthermore, the main bodies 28 of the extension members 20 may be preformed with a fixed curvature matching that of the interior of the retractor member 10. The particular shapes of the extension members 20 may vary, such that they may be symmetrical or asymmetrical, thereby allowing a surgeon to choose the shape that best fills the gap between the distal end 13 of the retractor member 10 and the bone, organ or body component in any given procedure. Examples of differing configurations, not to be taken as limiting, are shown in FIGS. 1, 7, 8 and 9. The dimensions of the extension members 20 may vary in height or width, such that for example one extension member 20 may extend a short distance axially but cover a large distance circumferentially, or vice versa. As shown in FIG. 7, the extension members 20 may be provided with teeth 24, slots 25 or other surface or body elements to better secure the tissue at the distal end 13 of the retractor member 10 to prevent creep, herniation or intrusion. As shown in FIG. 8, the extension members 20 may be provided with a distal lip member 26 for this same purpose.

Mounting means 30 are provided to affix or attach one or more extension members 20 in a fixed, non-moving, manner at or adjacent the distal end 13 of the retractor member 10, while the retractor member 10 is positioned within the patient, such that the extension members 20 extend beyond the distal end 13. Multiple extension members 20 may be abutted or overlapped if necessary. Mounting means 30 may comprise any suitable affixation mechanism, although a mechanical interlock is preferred over adhesive bonding or the like. The mounting means 30 should secure the extension member 20 with sufficient retention such that the extension member 20 will not be dislodged during the surgical procedure or upon removal of the retractor member 10.

Mounting means 30 may comprise spring-biased or clip mechanisms or other similar suitable means for mounting the extension members 20 to the retractor member 10. A preferred mounting means 30 comprising one or more generally J- or U-shaped clip or hook members 33 is shown in FIGS. 1 through 9, where the clip member 33 is sized and spaced a selected distance from the main body 28 of the extension member 20 so as to securely receive the edge of the distal end 13 of the retractor member 10, the clip member 33 preferably being either biased outwardly when the extension member 20 is brought upward onto the edge of the distal end 13 of the retractor member 10 or being pulled against the retractor member 10 when the extension member 20 is flexed to adopt the curve of the retractor member 10. The provision of plural clip members 33 on a single extension member 20, as shown in FIG. 7, acts to prevent undesired pivoting or translation of the extension member 20 relative to the retractor tube 10 after affixation.

Figure 11:
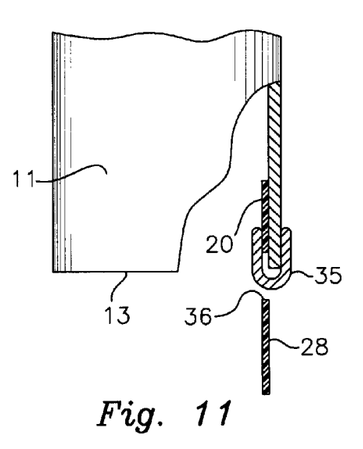
FIG. 11 is a view of an alternative embodiment for the extension member and mounting means, where a separate U-clip member is employed.

Still another embodiment for the extension member 20 and mounting means 30 is shown in FIG. 11, where the extension member 20 is provided with a slot or aperture 36 that receives a separate U-shaped clip member 35 that is mounted onto the distal end 13 of the retractor tube 10. With this embodiment, the extension member 20 can be positioned without first over-advancing the extension member 20 beyond the distal end 13 and then retracting to seat the clip member 33.

Figure 9:
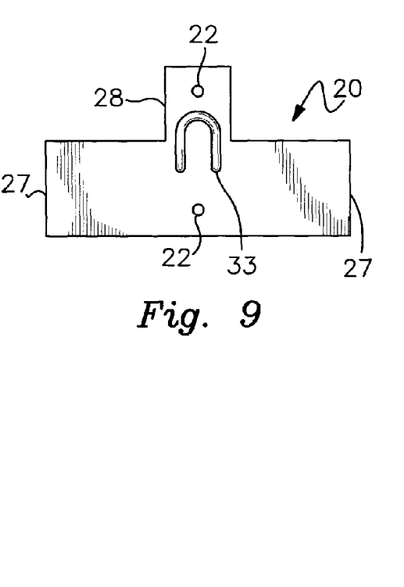
FIG. 9 is a front view of another alternative embodiment of the extension member having extended lateral members.

Another embodiment for the extension member 20 is shown in FIG. 9, where the extension member 20 is provided with lateral wing members 27 that greatly extend the lateral dimension of the extension member 20. With this configuration it is easy to overlap multiple extension members 20. Furthermore, such a configuration is useful for application to retractors of the spreadable blade type, since by their nature axially oriented gaps are created between the arms or blades of the retractor when such arms are expanded.

Figure 1:
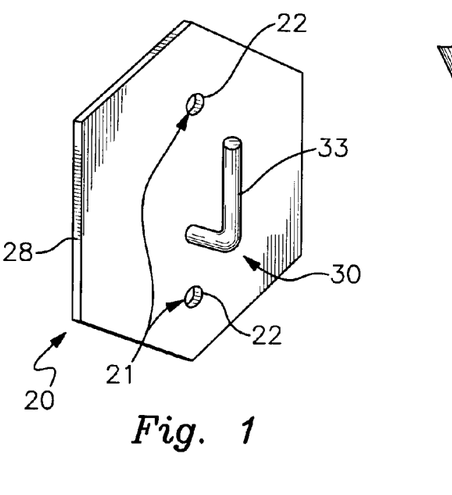
FIG. 1 is a perspective view of an alternative embodiment of the extension member having a mounting clip.
Figure 2:
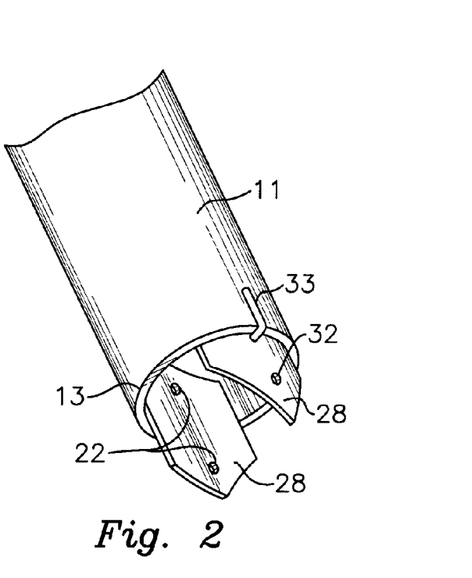
FIG. 2 is a perspective view of the distal end of an alternative embodiment tubular retractor having a pair of the extension members of FIG. 1 mounted thereto.
Figure 3:
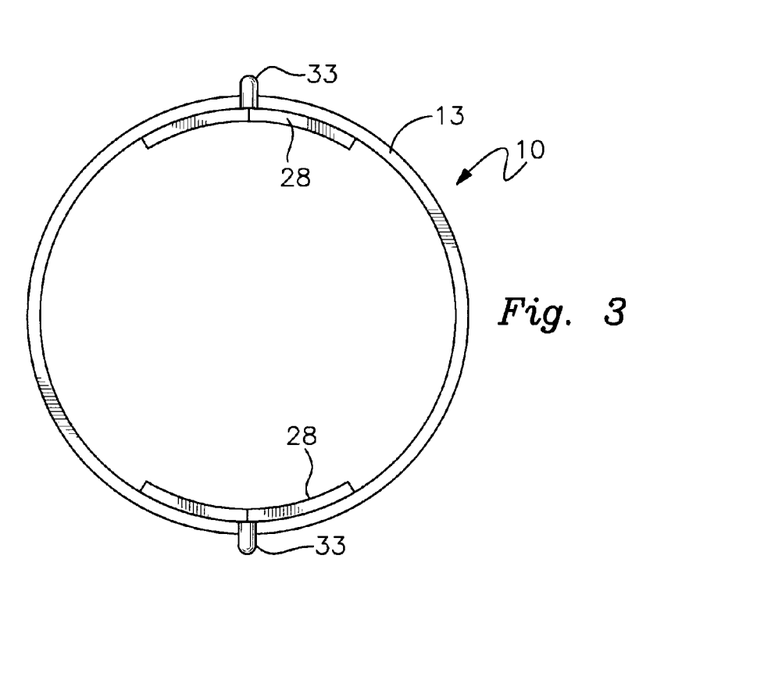
FIG. 3 is an end view of the distal end of the tubular retractor of FIG. 2.
Figures 4, 5:
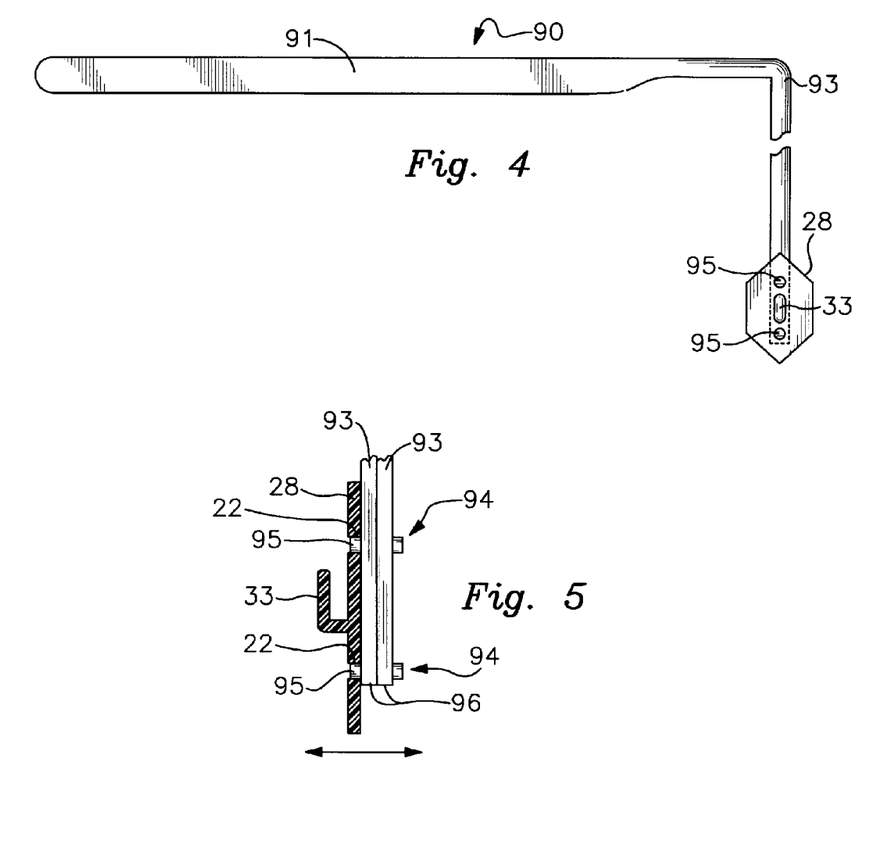
FIG. 4 is a side view of an applicator tool for positioning the expansion members.
FIG. 5 is a partial view of the end of the applicator tool, having a single extension member shown in cross-section and retained thereby.
Figure 6:
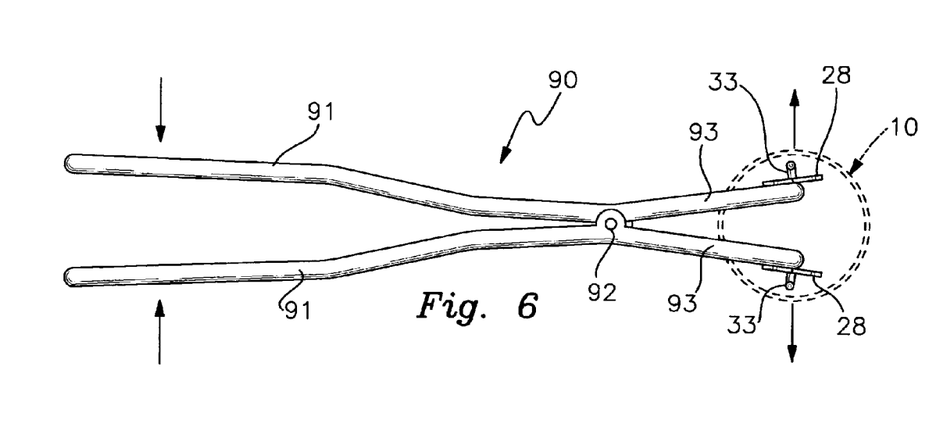
FIG. 6 is a top view showing a pair of extension members positioned within a tubular retractor prior to connection to the retractor.

Grasping forceps may be utilized to position the extension members 20 within the retractors members 10, but preferably specially adapted extended tools, forceps or similar grasping instruments are provided to attach the extension member 20 to the retractor member 10 after the retractor member 10 has been inserted into the body. A representative applicator tool 90 is illustrated in FIGS. 4 through 6, wherein the tool 90 is designed such that the extension member 20 is pressed against the interior wall of the retractor member 10 by squeezing the handles 91, the applicator tool 90 being spring biased so as to remain in the closed position until force is applied to the handles 91. The handles 91 are pivotally joined by pivot means 92 to L-shaped arm members 93, the length of the L-shaped arms 93 being greater than the length of the retractor member 10. Extension member retention means 94 are disposed adjacent or near the distal end 96 of the arms 93. The extension member retention means 94 as shown comprise pin members 95 that are received within tool apertures 22 disposed in the extension members 20. For the embodiment of the extension member 20 shown in FIGS. 1 through 7 and 9, the extension member 20 is inserted through the distal end 13 a sufficient distance for the clip member 33 to clear the distal end 13, then the extension member 20 is retracted to seat the clip member 33 on the distal end 13 of the retractor member 10.

Alternatively, the tool connector means 21 of the extension members 20 may comprise internally extending grasping projections or nubs 23, as shown in FIG. 8, such that conventional forceps or the like may be utilized to grasp and place the extension member 20. In a different embodiment, a bayonet-type applicator tool may be utilized to position the extension member 20, the bayonet-type applicator tool having an axially offset handle portion to allow visualization within the retractor member 10.

Figure 10:
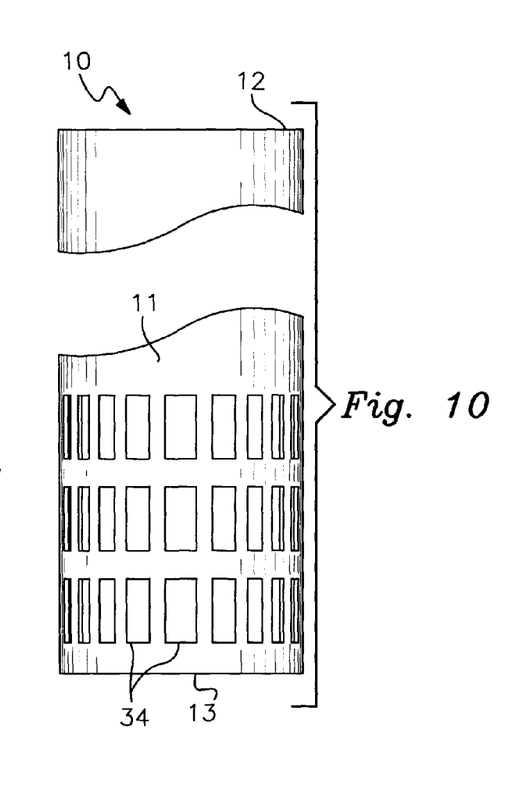
FIG. 10 is a view of an alternative embodiment for the tubular retractor having a plurality of grid apertures to receive the extension members.
Figure 12:
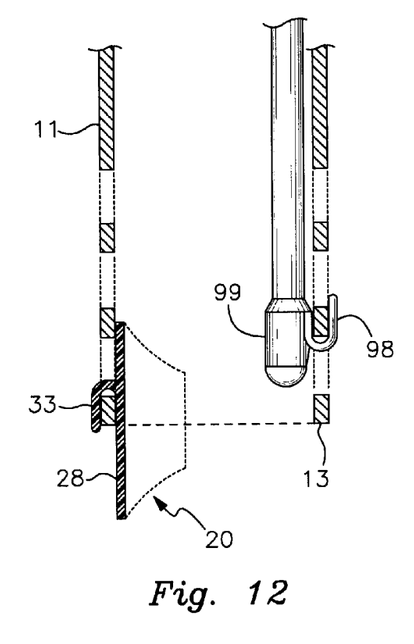
FIG. 12 is a cross-sectional view of the embodiment of FIG. 10, showing attachment of an extension member and an additional accessory to a fenestrated retractor.

The embodiments of the extension members shown in FIGS. 1 through 9 and in FIG. 11 are advantageous in that standard retractor members 10 currently in production do not need to be altered, since the extension members 20 are clipped onto the distal end 13 of the tubular retractor. In an alternative embodiment of the retractor member 10, as shown in FIG. 10, a fenestrated retractor member 10 comprises a large number of grid apertures 34, which may comprise various shapes, patterns and concentrations, such that the clip members 33 of the extension members 20 can be positioned at multiple locations. The clip members 33 may extend in any direction, including the distal, proximal or lateral directions. At least some of the grid apertures 34 are axially spaced along the retractor member 10, such that the grid apertures 34 are not equidistant from the distal end 13. These grid apertures 34 may extend the entire length of the retractor member 10. With this configuration the extension members 20 can be inverted such that the clip members 33 extend distally, which may enable better placement of the extension members in certain circumstances, as shown in FIG. 12. Additionally, other accessories 99 such as light sources, scopes, suctions, irrigators, etc. may be mounted into the grid apertures 34 in similar manner using clip members 98, with the clip members 98 extending in any direction, including the distal, proximal or lateral directions. The clip members 98 may be removable attachments to the accessories 99 or manufactured to be an integral member. Both of these embodiments may be incorporated into either tubular or blade retractors.

Figure 13:
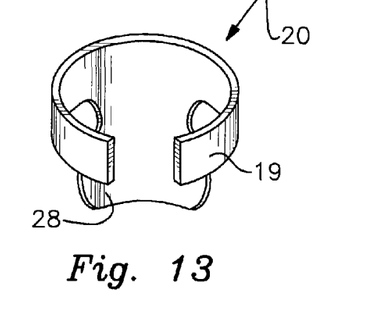
FIG. 13 is a perspective view of an alternative embodiment of the extension member, where the extension member is maintained within a tubular retractor by friction or biasing forces.
Figure 14:
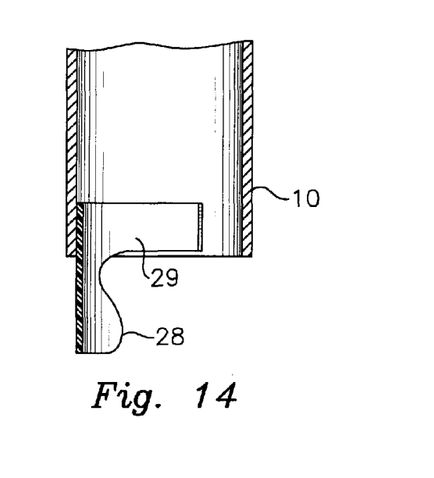
FIG. 14 is a partial cross-sectional view of the extension member of FIG. 13 shown positioned within a tubular retractor.
Figure 15:
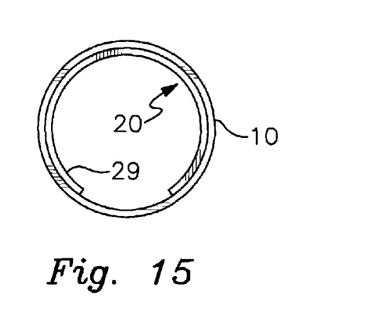
FIG. 15 is a top view of the extension member of FIG. 13 shown positioned within a tubular retractor.
Figure 16:
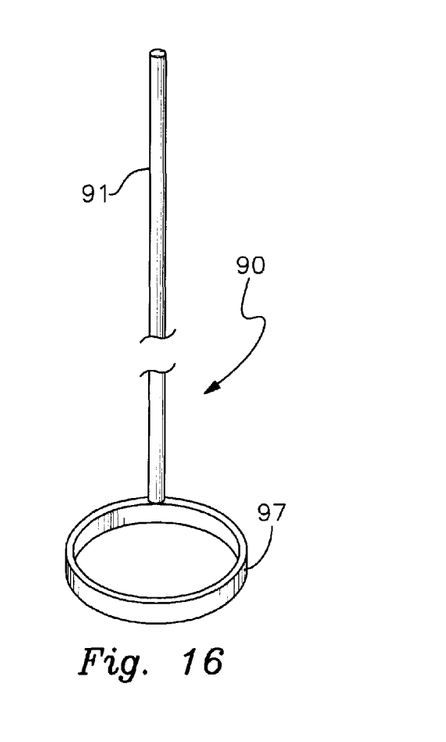
FIG. 16 is a view of an insertion or applicator tool for the extension member of FIG. 13.

Another alternative embodiment for the extension member 20 is shown in FIGS. 13 through 15. In this embodiment, the extension member 20 is retained within the tubular retractor member 10 by frictional or biasing forces. The extension member 20 comprises a shielding main body 28 depending from a slotted annular collar or ring member 29. The shape of the main body 28 may vary. The collar member 29 is sized such that its outer diameter matches that of the inner diameter of the tubular retractor member 10 within a small tolerance, such that the extension member 20 can be advanced down the interior of the retractor member 20 and is retained in the desired location at the distal end 13 by frictional forces, or preferably is sized and configured such that the ends of the slotted collar member 29 must be compressed slightly in order for the extension member 20 to be inserted into the retractor member 10, whereby biasing forces retain the extension member 20 at the desired location. The extension member 20 may be shaped much less circular than shown in the drawings in the neutral state, depending on the range of flexation inherent in the material of construction. In the case of a pure frictional fit, the collar member 29 may be non-slotted, i.e., comprising a full 360 degree circle. An alternative insertion or applicator tool 90 is shown in FIG. 16, the tool 90 comprising an elongated handle 91 connected to a ram member 97, which is annular as shown but may comprise a cylinder or other shape.

Preferably, the invention is provided as a kit comprising multiple extension members 20 of varying sizes and configurations, along with the applicator tool 90 and a depth gauge, such that the configuration of the distal end 13 of any standard retractor member 10 can be reconfigured as needed to prevent tissue creep.

The methodology of the invention comprises the steps of inserting a retractor member 10 into the body of a patient, this step being performed in standard manner. The surgeon then accesses the situation at the distal end 13 of the retractor member 10 to determine whether undesirable tissue creep is occurring or is likely to occur during the procedure. To preclude or minimize such tissue creep, the surgeon selects an appropriately sized and shaped extension member 20, inserts it into interior of the retractor member 10 using an appropriate applicator or insertion tool 90, and secures it to or adjacent the distal end 13 of the retractor member 10 in any of the manners discussed above. If necessary, multiple extension members 20 can be positioned at different points about the distal end 13, with the extension members 20 abutting, overlapping or separated. The extension members 20 may be repositioned or removed as necessary during the surgical procedure. Upon completion of the procedure, the extension members 20 may be detached and removed prior to removal of the retractor member 10, or may be left in place and removed in combination with the retractor member 10.

It is contemplated that equivalents and substitutions to certain elements set forth above may be obvious to those skilled in the art, and thus the true scope and definition of the invention is to be as set forth in the following claims. It is further expressed that the above examples and illustrations are meant to be representational rather than limiting in nature.

I claim:

1. The combination of a retractor member and a plurality of extension members;
    said retractor member comprising an elongated tubular main body and a distal end;
    each of said extension members comprising a main body and mounting means for removably mounting said extension member in a fixed, non-moving, position on said distal end of said retractor member after said retractor has been positioned within a patient, said mounting means comprising a clip member disposed on said extension member;
    whereby each of said extension members is mountable on said retractor member such that said distal end is received by said clip member and such that at least part of said main body extends beyond said retractor distal end such that said extension member minimizes or precludes tissue creep at said distal end of said retractor;
    wherein said mounting means comprises a slot disposed on said main body of said extension member and a U-shaped clip member positioned within said slot.

2. The combination of a retractor member and a plurality of extension members;
    said retractor member comprising an elongated tubular main body and a distal end;
    each of said extension members comprising a main body and mounting means for removably mounting said extension member in a fixed, non-moving, position on said distal end of said retractor member after said retractor has been positioned within a patient, said mounting means comprising a clip member disposed on said extension member;
    whereby each of said extension members is mountable on said retractor member such that said distal end is received by said clip member and such that at least part of said main body extends beyond said retractor distal end such that said extension member minimizes or precludes tissue creep at said distal end of said retractor;
    wherein said retractor is provided with a plurality of grid apertures, at least some of said grid apertures being axially spaced such that not all said grid apertures are equidistant from said distal end.

3. The combination of claim 2, wherein said mounting means comprises a U-shaped clip member disposed on said main body of each said extension member.

4. The combination of claim 2, wherein said mounting means comprises a J-shaped clip member disposed on said main body of each said extension member.

5. The combination of claim 2, wherein said mounting means comprises a slot disposed on said main body of said extension member and a U-shaped clip member positioned within said slot.

6. The combination of claim 2, wherein said main body of said extension member is curved.

7. The combination of claim 2, wherein said main body of said extension member is generally planar and is composed of a flexible material.

8. The combination of a retractor member and a plurality of extension members;
    said retractor member comprising an elongated tubular main body and a distal end;
    each of said extension members comprising a main body and mounting means for removably mounting said extension member in a fixed, non-moving, position on said distal end of said retractor member after said retractor has been positioned within a patient, said mounting means comprising a clip member disposed on said extension member;
    said extension member further comprising tool connector means for temporarily connecting said extension member to an applicator tool, said applicator tool comprising a pair of handles connected by pivot means to a pair of L-shaped arms, and extension member retention means disposed on said L-shaped arms to temporarily retain said extension members for mounting to said retractor member;
    whereby each of said extension members is mountable on said retractor member such that said distal end is received by said clip member and such that at least part of said main body extends beyond said retractor distal end such that said extension member minimizes or precludes tissue creep at said distal end of said retractor.

9. The combination of claim 8, wherein said mounting means comprises a U-shaped clip member disposed on said main body of each said extension member.

10. The combination of claim 8, wherein said mounting means comprises a J-shaped clip member disposed on said main body of each said extension member.

11. The combination of claim 8, wherein said main body of said extension member is curved.

12. The combination of claim 8, wherein said main body of said extension member is generally planar and is composed of a flexible material.

13. The combination of claim 8, wherein said tool connector means comprises at least one aperture disposed in said extension member.

14. The combination of claim 8, wherein said tool connector means comprises a projection.

15. The combination of claim 8, said extension member further comprising teeth.

16. The combination of claim 8, said extension member further comprising a curved lip.

17. The combination of claim 8, said extension member further comprising lateral wings.

18. The combination of claim 8, wherein said extension members have varying configurations and sizes.

19. The retractor extension member of claim 8, wherein said main body is composed of a relatively rigid central portion and a pair of relatively flexible lateral portions.

20. The combination of claim 8, wherein said tool connector means comprises at least one aperture disposed in said extension member, and wherein said extension member retention means comprise at least one pin that is received by said at least one aperture.

* * * * *